(12) United States Patent
Thevenet et al.

(10) Patent No.: US 11,383,053 B2
(45) Date of Patent: Jul. 12, 2022

(54) MEDICAL DEVICE FOR OLFACTORY STIMULATION

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE CLAUDE BERNARD LYON 1, Villeurbanne (FR); UNIVERSITE JEAN MONNET SAINT ETIENNE, Saint Etienne (FR)

(72) Inventors: Marc Thevenet, Lyons (FR); Patricia Viret, Lyons (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); UNIVERSITE CLAUDE BERNARD LYON 1, Villeurbanne (FR); UNIVERSITE JEAN MONNET SAINT ETIENNE, Saint Etienne (FR)

( * ) Notice: Subject to any disclaimer, the term of this patent is extended or adjusted under 35 U.S.C. 154(b) by 857 days.

(21) Appl. No.: 16/074,337

(22) PCT Filed: Feb. 2, 2017

(86) PCT No.: PCT/EP2017/052256
§ 371 (c)(1),
(2) Date: Jul. 31, 2018

(87) PCT Pub. No.: WO2017/134166
PCT Pub. Date: Aug. 10, 2017

(65) Prior Publication Data
US 2021/0178096 A1    Jun. 17, 2021

(30) Foreign Application Priority Data

Feb. 2, 2016    (EP) ..................... 16153961

(51) Int. Cl.
*A61M 16/00*    (2006.01)
*A61M 16/20*    (2006.01)
(Continued)

(52) U.S. Cl.
CPC ......... *A61M 16/0063* (2014.02); *A61G 11/00* (2013.01); *A61M 16/202* (2014.02);
(Continued)

(58) Field of Classification Search
CPC .................. A61M 16/0063; A61M 16/202; A61M 11/00; A61M 21/0094; A61M 2021/0016;
(Continued)

(56) References Cited

U.S. PATENT DOCUMENTS

| 4,934,386 A | 6/1990 | Walker et al. |
| 6,325,475 B1 * | 12/2001 | Hayes ..................... A61B 5/00 128/203.11 |

(Continued)

FOREIGN PATENT DOCUMENTS

| DE | 20 2004 004316 U1 | 6/2004 |
| WO | 96/14792 A1 | 5/1996 |
| WO | 96/28195 A1 | 9/1996 |

*Primary Examiner* — Steven O Douglas
(74) *Attorney, Agent, or Firm* — WCF IP

(57) ABSTRACT

The invention relates to a device for olfactory stimulation of a patient with a plurality of scents, said device comprising: —a source (2) of a carrier gas (G); —a plurality of scent odorization circuits, each odorization circuit (4) comprising: —a container (18) containing an odorous volatile substance (V), —a container inlet line (26), provided with a container inlet valve (28), connecting an inlet (30) of said container with said source of carrier gas, and —a container outlet line (36), provided with a container outlet valve (38), connecting (Continued)

an outlet (40) of said container with an exit line (12); —a control unit (8), configured to control said container inlet valve and container outlet valve according to a medical protocol.

13 Claims, 1 Drawing Sheet

(51) Int. Cl.
    *A61G 11/00*     (2006.01)
    *A61M 21/00*     (2006.01)

(52) U.S. Cl.
    CPC . *A61M 21/0094* (2013.01); *A61M 2021/0016* (2013.01); *A61M 2205/07* (2013.01); *A61M 2205/3334* (2013.01); *A61M 2205/3355* (2013.01); *A61M 2205/502* (2013.01); *A61M 2209/08* (2013.01); *A61M 2230/06* (2013.01); *A61M 2230/42* (2013.01); *A61M 2240/00* (2013.01)

(58) Field of Classification Search
    CPC ...... A61M 2205/07; A61M 2205/3334; A61M 2205/3355; A61M 2205/502; A61M 2209/08; A61M 2230/06; A61M 2230/42; A61M 2240/00; A61G 11/00
    See application file for complete search history.

(56) References Cited

U.S. PATENT DOCUMENTS

| | | |
|---|---|---|
| 6,702,767 B1 | 3/2004 | Douglas et al. |
| 2013/0127620 A1 | 5/2013 | Siebers et al. |
| 2015/0126803 A1 | 5/2015 | Rapoport |

* cited by examiner

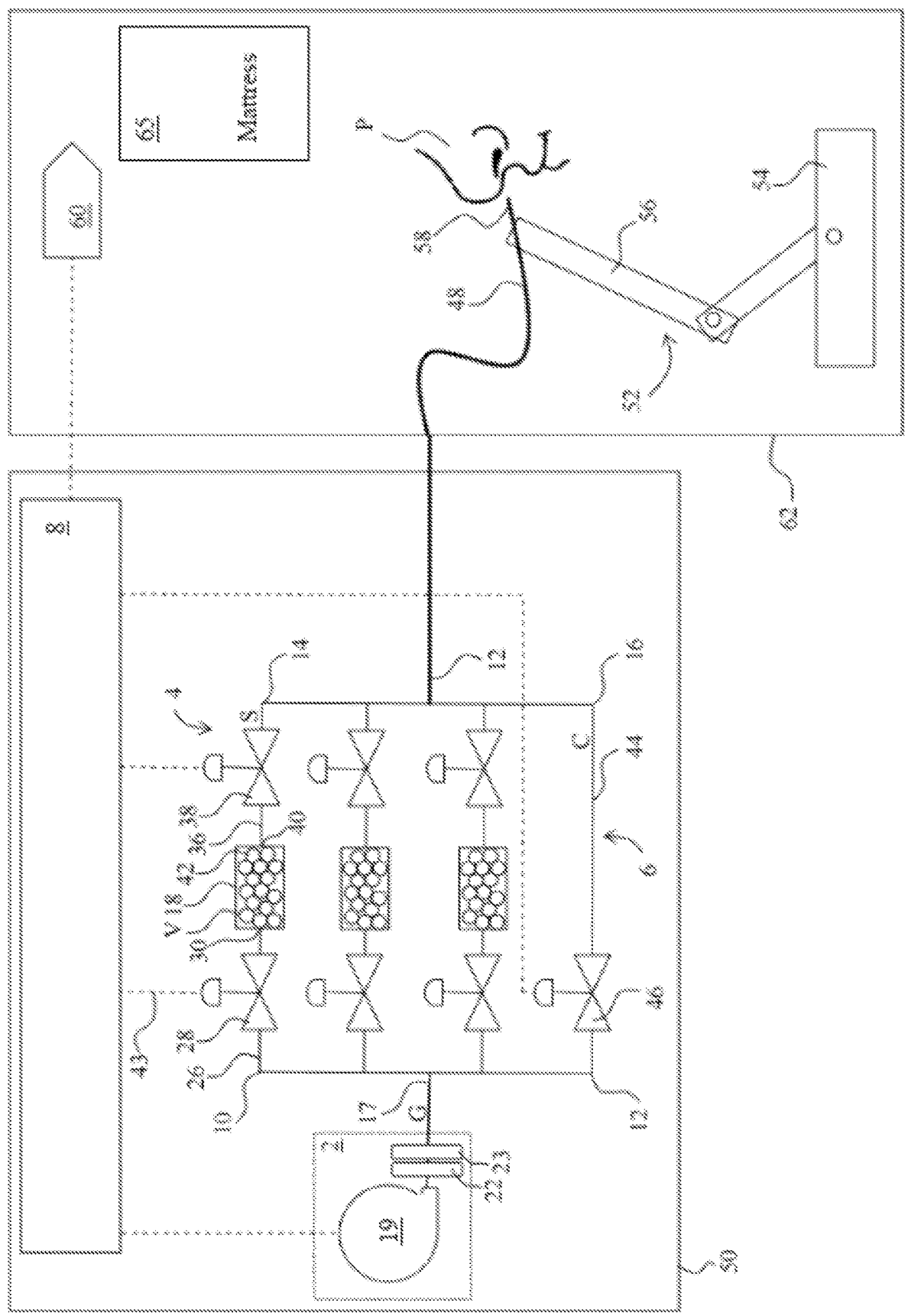

MEDICAL DEVICE FOR OLFACTORY STIMULATION

TECHNICAL DOMAIN

The invention concerns a medical device for olfactory stimulation. This device delivers a plurality of scents with precise flow rates and durations, preferably according to preprogrammed flexible sequences.

STATE OF THE ART

Apnea of premature newborn infants is a serious disease. This disease is usually treated with drugs. However, these drugs are not always efficient. In addition, they may induce undesirable effects.

The aim of the present invention is to provide a new solution to treat apnea which could supplement, or even replace the pharmacological treatments, and thus avoid said undesirable effects.

SUMMARY OF THE INVENTION

To this end, the invention provides a device for olfactory stimulation with a plurality of scents, said device comprising:
- a source of a carrier gas, preferably a medical gas;
- a plurality of scent odorization circuits, each odorization circuit comprising:
  - a container containing an odorous volatile substance,
  - a container inlet line, provided with a container inlet valve, connecting an inlet of said container with said source of carrier gas, and
  - a container outlet line, provided with a container outlet valve, connecting an outlet of said container with an exit line;
- a control unit, configured to control said container inlet and container outlet valves according to a medical protocol.

Scents have been successfully tested to treat diseases requiring a cerebral awaking, in particular to treat apnea, in particular in premature newborn infants or neonates, and sleep apnea in adults.

As it will described in further details, the inlet and outlet valves on the upstream and downstream sides of each containers advantageously of a device according to the invention allows for the delivery of precisely defined puffs of scents.

The device therefore enables the implementation of precise medical protocols. Medical protocols may in particular be intended to olfactory stimulate premature newborn infants in incubators, hospitalized in intensive neonate care units in order to decrease the occurrence of apnea.

In addition, the device uses simple means, such as containers, valves, source of compressed air. It is therefore cost effective.

Preferably, a device according to the invention presents one or several of the following optional characteristics:
- The device comprises a cleaning circuit to extract gas located in the odorization circuits downstream their respective container outlet valves. The purity of the scents is thereby increased since the cleaning avoids inter-odorant pollution. Advantageously, successive olfactory stimulations are maintained as qualitatively distinct;
- The carrier gas is a medical gas. The risk of contamination is thereby decreased;
- The source of carrier gas is configured to provide a flow (exiting form said source) greater than 300 ml/min and/or less than 500 ml/min through any of said containers. The device is advantageously well-adapted for a plurality of the treatments;
- The containers have a shape of a "U" and contain a substrate, preferably in the form of pellets, on which an odorant is adsorbed and from which the said volatile substance can be extracted by the carrier air flow. This shape makes the filling of the container easier. It also proved to be optimal for the extraction of volatile substance by the carrier gas;
- At least two, preferably at least three containers contain different volatile substances. The variety of possible treatments is thereby increased. Also, sensory habituation is thereby avoided;
- At least one, preferably at least two, preferably at least three containers contain different volatile substances, said volatile substances being chosen in the group consisting of (R)-(−)-Carvone, Vanillin, and (R)-(+)-Limonene. These volatile substances are indeed particularly efficient for the treatment of sleep apnea;
- The exit line is common to all the odorization circuits, and preferably to all the odorization circuits and the cleaning circuit. The structure of the device is thereby made much simpler;
- All the odorization circuits and the control unit are included in a casing, the largest dimension of the casing being less than 50 cm. The device may thereby become easily transportable;
- The medical protocol includes stimulation periods, during which a odorization circuit is activated, and cleaning periods, during which the cleaning circuit is activated while all the odorization circuits are deactivated;
- A stimulation period, preferably any stimulation period, lasts less than 10 s, and/or a cleaning period, preferably any cleaning period, lasts less than 2 s;
- The device comprises at least one sensor enabling measurement of a physiological parameter of the patient, and an analysis module able to analyze the data provided by said sensor, and to generate a diagnostic of the patient health and/or an evaluation of the efficiency of the medical protocol and/or to modify said medical protocol depending on said diagnostic and/or evaluation;
- The device is configured so that the mixture of the carrier gas and of the volatile substance which exits from said exit line is gaseous. Advantageously, no particles are sprayed, which improves the accuracy of the treatment.

The invention also concerns an incubator comprising a chamber to place a premature newborn infant, and, preferably outside said chamber, a device according to the invention.

The invention also concerns the use of a device according to the invention to treat a disease requiring a cerebral awaking, like coma or dysphagia, to treat sleep apnea, in particular by children and premature newborn infants.

BRIEF DESCRIPTION OF THE DRAWINGS

The invention will be better understood from the reading of the detailed description that follows, with reference to exemplary and non-limiting embodiments thereof, and by the examination of the appended drawing, in which FIG. 1 shows in a synoptic diagram of a device according to a preferred embodiment of the invention.

Definitions

A «patient» is a person receiving a scent from a device according to the invention. A patient may have a disease or not.

"Upstream" and "downstream" are relative to the flow of gas when the device is in service.

For clarity, the "volatile substance" is an odorous material in a container, whereas a "scent" is a mixture of gaseous molecules of said volatile substance with the carrier gas.

DETAILED DESCRIPTION OF A PREFERRED EMBODIMENT

FIG. 1 represents an example of a device according to the invention.

This device comprises a source 2 of a gas G, preferably a medical gas, three parallel odorization circuits 4, a cleaning line 6, and a control unit 8.

The source of gas feed the inlet end 10 of each odorization circuit and the inlet end 12 of the cleaning line.

The outlets 14 of the odorization circuits 4 and the outlet 16 of the cleaning circuit 6 are in fluid communication with a common exit line 12, intended to provide a scent S or a cleaning gas C to a patient.

The number of odorization circuits is preferably greater than 2, preferably greater than 3.

Preferably, the structures of the odorization circuits 4 are identical. For the sake of clarity, only one odorization circuit is therefore described.

Source of Gas

The source 2 of carrier gas provides, through a gas line 17, a carrier gas G to take some volatile substance as it comes into contact with said substance in a container 18 of a odorization circuit. The carrier gas G is preferably a medical gas.

It is preferably odorless. It is preferably air.

Air from the environment may be used if it is compatible with the state of the patient. In particular when the device is intended to be used at home, the source of gas may be the atmosphere.

The source of carrier gas may comprise a compressor 19 and/or a bottle of carrier gas under pressure. The gas line 17 may also be provided with a gas valve.

The carrier gas entering into a container is preferably at a pressure greater than 1.3 bar, preferably greater than 1.5 bar, preferably greater than 1.7 bar, and/or preferably less than 2.5 bar, preferably less than 2.3 bar. To this end, the source of carrier gas preferably includes a pressure regulator 22.

In the preferred embodiment, the source of carrier gas includes, in addition to the pressure regulator, and flow controller 23, preferably located downstream of the pressure regulator. The flow controller is preferably configured so that the flow through a container is greater than 200 ml/min, preferably greater than 300 ml/min, preferably greater than 400 ml/min, and/or less than 2000 ml/min, preferably less than 1000 ml/min, preferably less than 800 ml/min, preferably less than 600 ml/min, preferably less than 500 ml/min.

For premature newborn infants, the flow controller is preferably configured so that the flow through a container, which is ultimately delivered in the incubator, is between 300 ml/min and 500 ml/min.

Odorization Circuit

Each odorization circuit 4 comprises:
a container 18 containing an odorous volatile substance V,
a container inlet line 26, provided with a container inlet valve 28, connecting an inlet 30 of said container with the source of carrier gas, and
a container outlet line 36, provided with a container outlet valve 38, connecting an outlet 40 of said container with the exit line 12.

The container 18 is preferably a tube presenting a U-shape, the container inlet 30 and container outlet 40 being the openings at the ends of the two branches of the U. A U-shape has proved to be efficient and easy to handle when it is filled with pellets or granules.

The container 18 is preferably made of glass.

The container 18 preferably contains a substrate, preferably in the form of pellets or of granules 42, on which the odorous volatile substance is adsorbed. Such pellets or granules optimize the exchanges between the carrier gas and the volatile substance.

Preferably, the container does not contain any liquid. In particular, the substrate is preferably dry.

The substrate is preferably a polymer, preferably a polyethylene. A polyether block amide copolymer such as PEBAX® 2533 SA01 may be used as a substrate.

Preferably, the device comprises more than 2, preferably more than 3 containers 18 containing different volatile substances.

The volatile substance V is preferably adsorbed on said substrate. It may be adsorbed on the substrate.

The volatile substances are preferably different, depending on the container.

Preferably, at least one, preferably at least two, preferably three of the volatile substances are chosen in the group consisting of (R)-(−)-Carvone (CAS: 6485-40-1), Vanillin (CAS: 121-33-5), and (R)-(+)-Limonene (CAS: 5989-54-8).

The inlet of a container 18 is selectively in fluidic communication, through the respective container inlet valve 28, with the source of carrier gas.

The outlet of a container 18 is selectively in fluidic communication, through the respective container outlet valve 38, with the exit line 12.

The presence of a container outlet valve 38 downstream of each of said container 18 is particularly advantageous. Indeed, it enables a precise flow of a pure scent in the exit line, with a simple technology.

All the container inlet and container outlet valves are controlled by the control unit 8 through control lines 43, represented with a dashed line in FIG. 1. For clarity, only the control lines 43 of one odorization circuit are represented in FIG. 1

Cleaning Circuit

The cleaning circuit 6 is configured to extract the scent(s) remaining downstream of the container outlet valves after all the container outlet valves have been closed. Preferably, said remaining scents are extracted through the exit line 12.

The cleaning circuit 6 is preferably fed with air, preferably medical air. In particular, it is preferably fed by the source of carrier gas.

The cleaning circuit 6 preferably comprises a cleaning line 44 and a cleaning valve 46, inserted in the cleaning line and controlled by the control unit 8. The ends of the cleaning line 44 are connected to the source of carrier gas on the upstream end, and with the exit line on the downstream end. The cleaning circuit 6 is therefore parallel to the odorization circuits, i.e. is in fluid communication with the source of carrier gas on the upstream end, and with the exit line on the downstream end.

Exit Line

The exit line is preferably flexible. Preferably, it comprises or is a flexible tube, preferably made of Teflon®.

In the preferred embodiment, all the odorization circuits, and preferably the control unit and preferably the source of carrier gas are included in a casing 50. Preferably, the largest dimension of the casing 50 is less than 50 cm, preferably less than 40 cm, and preferably less than 30 cm.

The exit line has, at one end, an upstream end which is preferably common to all the odorization circuits, and, preferably, the cleaning circuit, and, at the other end, a downstream end 48 which, in service, deliver the scents to the patient.

The downstream end of the exit line preferably opens close to the nose of the patient. Depending on the patient, it may open at a distance less than 80 cm, less than 60 cm, less than 40 cm, less than 20 cm, less than 10 cm from the nose of the patient. However, the downstream end of the exit line is preferably spaced from the patient, i.e. not in contact with the patient, so that the patient can freely breathe.

The device preferably comprises a support 52 for the downstream end 48 of the exit line. Preferably, the geometry of the support 52 can be modified by a physician, preferably by hand. The support 52 may in particular comprise a base 54 and an arm, articulated on the base. The arm preferably comprises several branches 56 which are articulated on each other. The branches may be mobile by rotation and/or translation relative to the base and/or relative to each other.

In an embodiment, the downstream end 48 of the exit line is provided with a tube, preferably made in Teflon®, obstructed by a filtering plug 58, preferably in a sintered glass.

Control Unit

The control unit 8 is configured to control all the container inlet valves, container outlet valves, and cleaning valve according to a medical protocol. Preferably, the control unit 8 is also configured to control the source of carrier gas.

The control unit 8 preferably controls the container inlet valves and/or the container outlet valves and/or the cleaning valves through electric wires or through wireless communication means, i.e. electromagnetic signals.

The control unit is configured to open and close these valves independently. In particular, it controls the container inlet valve of an odorization circuit independently of the container outlet valve of this odorization circuit. It also controls independently the valves of the different odorization circuits.

The structure of the control unit may be conventional. It comprises a microprocessor controlling the valves according to a computer program stored in a memory. The memory also contains the medical protocol to parameterize the program.

The control unit preferably comprises an interface, in particular a screen and/or a keyboard, to enable communication with a human. The interface is preferably intuitive and user-friendly.

Preferably, the lengths of the stimulation periods, of the cleaning periods and of the idle periods, as well as the sequence of these periods may be determined with the interface.

A medical protocol specifies stimulation periods, during which at least one, preferably only one, of the odorization circuits must be activated, and cleaning periods, during which the cleaning circuit must be activated and all the odorization circuits must be deactivated.

The "activation" of a odorization circuit corresponds to the opening of the container inlet and outlet valves of this circuit.

The "deactivation" of a odorization circuit corresponds to the closing of the container outlet valve of this circuit, and preferably of the container inlet valve of this circuit. The closure of the container valves avoids any delivery of the volatile substance contained in this container into another odorization circuit.

The "activation" and "deactivation" of the cleaning circuits correspond to the opening and closing, respectively, of the cleaning valve.

Preferably, a stimulation period lasts more than 3 s and/or less than 10 s, preferably less than 7 s, preferably less than 6 s. The efficiency of the treatment is improved. In particular, such short stimulation periods are sufficient to stimulate the olfactory system and the autonomic nervous system, but avoid any contamination of the incubator.

Preferably, a cleaning period lasts more than 0.5 s and/or less than 2 s, preferably less than 1.5 s.

Preferably, a cleaning period is programmed to systematically occur between the diffusing of two different volatile substances.

Preferably, a cleaning period starts when a stimulation period ends.

Between the end of a cleaning period and the beginning of the next stimulation period, an idle period is possible. For an optimal efficiency, idle periods which last more than 20 s, preferably more than 30 s, preferably more than 40 s, preferably more than 50 s, and/less than 120 s, preferably less than 90 s, preferably less than 70 s are preferred.

Preferably, the control unit 8 is also configured to only activate the source of carrier gas during the stimulation and cleaning periods. The "activation" of the source of carrier gas corresponds to the injection of the carrier gas into the odorization circuits and/or cleaning circuit.

In the preferred embodiment, the control unit also comprises sensors 60 enabling measurement of physiological parameters of the patient, in particular related to his breath or heartbeat. In the preferred embodiment, the control unit also comprises an analysis module able to analyze the data provided by said sensors, and possibly the applied medical protocol, so as to generate a diagnostic of the patient health and/or an evaluation of the efficiency of the medical protocol. In an embodiment, the control unit is configured to modify said medical protocol depending on said diagnostic and/or evaluation.

The sensors and analysis module preferably monitor and record, in continuous and uninterrupted real-time, the physiological parameters of the patient, and the moments and durations of the applied olfactory stimulations.

Isolating Means

A device of the invention preferably comprises isolating means, i.e. means enabling a physical isolation of the patient. In particular, the isolating means may be a chamber 62 in which the patient may stay. A mattress 65 may be provided in the chamber.

Preferably, the source of carrier gas, the containers, the container inlet and outlet valves are outside said chamber, as represented on FIG. 1.

The isolating means are preferably an incubator for premature newborn infants.

Operation

The patient may be a premature newborn infant. He is placed in an incubator according to the invention. The device according to the invention may then be operated as follows.

Pellets on which are adsorbed carvone, vanillin, and limonene are poured into respective U-shaped containers. The inlets of these containers are connected to the respective container inlet lines 26. The outlets of these containers are connected to the respective container outlet lines 36.

Depending on the treatment, the physician programs the device, through its interface.

Initially, all the container inlet and outlet valves are closed, and the cleaning valve is closed.

When a stimulation period occurs, the corresponding scent is prepared form the volatile substance in a container of an odorization circuit, for instance vanillin. To this end, the source of the carrier gas is activated. For instance the compressor 19 is started. The container inlet and outlet valves of the odorization circuit are opened. The pressor regulator and the flow controller then regulate the pressure and flow of carrier gas into the container.

As it goes through the container, the carrier gas drives volatile odorous molecules of the substance V. The mixture of the carrier gas and of the volatile substance is a gaseous scent which is conveyed to the downstream end of the exit line.

A droplet of an odoriferous substance which would be deposited on the skin of the patient would potentially have a negative impact on the health of the patient. In addition, when deposited in the environment of the patient, such a droplet would emit an odor for a long time, which would interfere with the treatment. It might also be oxidized, and change the emitted odor. It is therefore an important advantage when the mixture of the carrier gas and of the volatile substance which exits from said exit line is gaseous, i.e. does not contain any droplets as a nebulisate.

The scent exits the exit line to enter into the incubator through a Teflon® tube ended with a filter, preferably a sintered glass plug.

The stimulation period is preferably a pulse, and preferably lasts between 5 and 10 s.

At the end of the stimulation period, the container inlet and outlet valves of the odorization circuit are closed, preferably simultaneously. The cleaning valve is then opened. This opening preferably immediately follows the closing of the container outlet valve.

The carrier gas is then conveyed to the incubator. It cleans the part of the odorization circuit which is downstream the container outlet valve.

After about 1 s of cleaning, the carrier gas entering into the incubator substantially does not contain any volatile substance any more.

The device is then ready for another delivery of an odorous volatile substance, which may be the same or be different than the previously delivered substance, for instance carvone, depending on the chosen medical protocol.

Between the end of the cleaning period and the beginning of the next stimulation period, an idle period is possible. Preferably, the source of carrier gas is deactivated so that no more gas is delivered into the incubator.

The frequencies of the stimulation periods and theirs durations are variable, and determined by the medical protocol. They may also be adjusted by the physician.

Preferably, a cleaning period always follows any stimulation period.

Scientific publications have reported the efficiency of olfactory stimulating treatment on the sleep respiration. Tests have demonstrated the efficiency of a device according to the invention to apply such a treatment.

In the preferred embodiment, the sensors 60 measure physiological parameters of the patient, and these measures are analyzed by the analysis module.

The medical protocol is preferably adapted depending on the results of this analysis. The analysis may also be used to gather information about the disease itself, so as to improve its treatment.

For an optimal treatment, the device is preferably programmed to works continuously (i.e. with a succession of stimulation periods, cleaning periods and idle periods), for periods of time during more than 3 hours, preferably more than 6 hours, preferably more than 12 hours, preferably more than 24 hours.

It now appears clearly that a device according to the invention enables a very effective and well-controlled delivery of different scents, and in particular of pure scents.

In addition, it is technically simple, which means can be fabricated and operated with low costs.

Of course, the invention is not limited to the embodiments which were disclosed and represented, only provided as illustrative and non-limitative examples. In particular, a device according to the invention may be used in a hospital, but also in the patient's home.

The invention claimed is:

1. Device for olfactory stimulation of a patient with a plurality of scents, said device comprising:
    a chamber in which said patient may stay, a mattress being provided in said chamber,
    a source of a carrier gas;
    a plurality of scent odorization circuits, each odorization circuit comprising:
        a container containing an odorous volatile substance,
        a container inlet line, provided with a container inlet valve, connecting an inlet of said container with said source of carrier gas, and
        a container outlet line, provided with a container outlet valve, connecting an outlet of said container with an exit line;
    a control unit, configured to control said container inlet valve and container outlet valve according to a medical protocol, said container inlet and container outlet valves being controlled by the control unit through control lines,
    said device comprising a cleaning circuit to extract gas located in the odorization circuits downstream their respective container outlet valves, and the medical protocol including stimulation periods, during which an odorization circuit is activated, and cleaning periods, during which the cleaning circuit is activated while all the odorization circuits are deactivated.

2. Device according to claim 1, in which the carrier gas is a medical gas.

3. Device according to claim 1, in which the source of carrier gas is configured to provide a flow greater than 300 ml/min and less than 500 ml/min through any of said containers.

4. Device according to claim 1, in which the containers have a shape of a "U" and contain a substrate on which the odorant is adsorbed and from which said volatile substance is released.

5. Device according to claim 1, in which at least two containers contain different volatile substances.

6. Device according to claim 1, in which at least one container contains different volatile substances, said volatile substances being chosen in the group consisting of (R)-(−)-Carvone, Vanillin, and (R)-(+)-Limonene.

7. Device according to claim 1, in which the exit line is common to all the odorization circuits.

8. Device according to claim 1, in which all the odorization circuits, and the control unit are included in a casing, the largest dimension of the casing being less than 50 cm.

9. Device according to claim 1, in which a cleaning period lasts less than 2 s.

10. Device according to claim 1, comprising at least one sensor enabling measurement of a physiological parameter of the patient, and an analysis module able to analyze the data provided by said sensor, and to generate a diagnostic of the patient health and/or an evaluation of the efficiency of the medical protocol and/or to modify said medical protocol depending on said diagnostic and/or evaluation.

11. Device according to claim 1, configured so that the mixture of the carrier gas and of the volatile substance which exits from said exit line is gaseous.

12. A device according to claim 1, wherein said chamber is an incubator for premature new born infants.

13. A device according to claim 1, wherein each container has a shape of a "U" having two branches, each branch having a respective opening at an end of said branch, said container having a container inlet and a container outlet which are the openings at the ends of the two branches of the U.

* * * * *